United States Patent [19]

Hodosh

[11] 4,343,608

[45] Aug. 10, 1982

[54] COMPOUND AND METHOD FOR PRESERVING DENTAL PULP

[76] Inventor: Milton Hodosh, 72 Overhill Rd., Providence, R.I. 02906

[21] Appl. No.: 126,433

[22] Filed: Mar. 3, 1980

[51] Int. Cl.³ ............................................... A61C 5/02
[52] U.S. Cl. ..................................................... 433/224
[58] Field of Search ...................... 433/228, 224, 226

[56] References Cited

U.S. PATENT DOCUMENTS 3,863,006 1/1975 Hodosh .................................. 424/49
4,121,940 10/1978 Michel ................................ 433/224

*Primary Examiner*—Robert Peshock
*Attorney, Agent, or Firm*—Salter & Michaelson

[57] ABSTRACT

A compound and method for preserving dental pulp, the essential ingredient of said compound comprising potassium nitrate and the method comprising as its essential step the capping of the pulp with the aforesaid compound.

5 Claims, No Drawings

COMPOUND AND METHOD FOR PRESERVING DENTAL PULP

BACKGROUND AND SUMMARY OF THE INVENTION

The present invention relates to a compound and method for preserving and healing dental pulp.

The dental pulp is a delicate connective tissue abundantly interspersed with tiny blood vessels, unmyelinated nerves, lymphatics and embryonic connective tissue cells. In this respect the pulp is similar in its make-up to other connective tissues throughout the body in that it reacts to bacterial infection or to other stimuli with an inflammatory response. The pulp, however, has some unique anatomic features that alter the nature and course of this response. Specifically, the calcified walls of dentin act as a firm enclosure for the pulpal connective tissues which limits the amount of usual tissue swelling that occurs in the hyperemic and edematous phases of inflammation. The blood vessels that supply the pulp enter the tooth through tiny apical openings, and once the tooth root has calcified, it is impossible for a collateral blood supply to develop through the hardened dentin and penetrate this inflammed tissue. In other connective tissues throughout the body, a collateral circulation would readily develop in the presence of inflammation. The inaccessibility of pulp connective tissue to external treatment has generally precluded its continued survival even after a mild injury, and hence many pulps have been sacrificed for lack of a truly effective treatment.

Most pulpitis results from the progressive spread of dental caries in which bacterial infection of the pulp occurs. Pulpitis may also arise as a result of chemical irritation of the pulp, as is seen in exposed pulps to which some medicament is applied. This may also occur with intact pulps beneath deep cavities into which irritating filling material has been inserted. In such cases, these substances penetrate and traverse the dentinal tubules into the pulp. Pulpitis itself is caused by a variety of circumstances, each producing a deleterious effect on the dental pulp. It occurs frequently in a tooth with a large carious lesion or where the restoration is defective, and there has been recurrent caries.

Pain is elicited in the early stages of pulpitis, even when the inflammatory reaction involves only a part of the pulp. Cold sensitivity is usually most notable, and pain may persist even after the thermalstimuli has been eliminated. Sensitivity to both cold and heat is common in the presence of any type of pulpitis, and as more of the pulp becomes involved, the pain increases in intensity. The pain may be continuous and may even increase in severity due to changes in body position, such as bending over or lying down. When pulp tested, the tooth will exhibit extreme sensitivity when compared to the adjacent healthy teeth. This condition usually continues on to necrosis of the pulp and abscess formation with sensitivity ultimately being lost when pulp tested.

Severe pain is more likely to be present when the opening to the pulp is small. Pulpal pressure increases because the inflammatory exudate has no way to escape, and there is a rapid spread of inflammation throughout the pulp with resultant pain and necrosis. Until the necrosis extends beyond the pulp tissue within the root, the tooth is not particularly sensitive to percussion. When the opening to the pulp is large, the opportunity for a build-up of pressure is less. In such a case, the inflammatory process does not tend to spread as rapidly throughout the pulp and the pain experienced is of a dull, throbbing nature.

Prior to the present invention, there has not been a predictably successful treatment for pulpitis. In fact, the consensus has always been that once pulpitis occurs, the damage is irreparable, leading to abscess formation. If these teeth are to be retained, the pulps usually require extirpation, thorough cleansing, and sealing of the pulp chambers and root canals with a suitable material. Many medicaments have been tried to preserve the diseased pulpal tissues. Medicated cements, calcium hydroxide, zinc oxide and eugenol, steroids, antibiotics, etc. have been tried for this purpose but the success rate for these medications has been poor for the short term, and even less encouraging for the long term.

In accordance with the present invention, it has now been found that by adding a few drops of potassium nitrate to a zinc oxide-eugenol paste or other suitable vehicles, a compound results which when used for the capping of dental pulp prevents most pulp degeneration and abscess formation from occurring. The instant applicant has heretofore recognized the amazing effectiveness of potassium nitrate in connection with the treatment of other dental problems and reference is made to applicant's U.S. Pat. No. 3,863,006 dated Jan. 28, 1975, entitled "Method for Desensitizing Teeth" and U.S. Pat. No. 4,191,750 dated Mar. 4, 1980, entitled "Method for Treating Canker Sores". However, prior to the instant invention, it was not known that the use of potassium nitrate as one of the essential ingredients in a compound used for the capping of dental pulp would prevent most pulpal degeneration and abscess formation from occurring. In the GorgasDental Medicine publication cited in the aforesaid U.S. Pat. No. 4,191,750, it is suggested (on Page 262) that nitrate of potassium has been recommended for use in the incipient stages of alveolar abscess, being introduced into the pulp canal and secured by a temporary filling in the crown cavity of the tooth. However, the gist of the present invention is to cap the dental pulp with the potassium nitrate containing compound prior to any abscess formation, since once an abscess has started to form, the compound and treatment of the present invention is of little effect.

DESCRIPTION OF THE INVENTION

In carrying out the present invention, the decayed and pulp-involved teeth are first identified by clinical and X-ray examination, since teeth which are to be treated in accordance with the present invention do not have X-ray visible periapical pathology, and are not clinically sensitive to percussion. Local anesthesia is administered, cavity outline preparations performed, and the decay completely removed. The pulp exposures and near pulp exposures are then capped with a compound which may contain a zinc oxide-eugenol (oil of cloves) paste to which a few drops of a saturated aqueous solution of potassium nitrate has been added. More specifically, the zinc oxide, which is in powder form, is mixed with the eugenol until the desired consistency is obtained, and in practice it has been found that a mixture comprising 5 parts by weight eugenol and 40 parts by weight zinc oxide is effective. The saturated aqueous solution comprising potassium nitrate preferably comprises approximately 3 parts by weight of the compound. When the compound has hardened within the tooth, permanent restorations are placed thereover.

It has also been found that zinc polyacrylate cement provides an excellent vehicle for the aforesaid nitrates for pulp capping purposes. Zinc polyacrylate cements are used for the retention of crowns and bridge work and as bases under other restorations. The material is in the form a viscous liquid and powder. The liquid is approximately a 40% solution of polyacrylic acid in water, and the powder is mainly zinc oxide with a smaller amount of magnesium oxide. The polyacrylate acid as a binder for the unreacted zinc oxide particles. In accordance with the present invention, a few drops of water saturated postassium nitrate, when added to the cement, makes the resultant compound highly effective for preventing pulpal degeneration and abscess formation from occurring, when the compound is used as a cap for the dental pulp. The procedure may be simplified by using freeze dried zinc polyacrylate cement, such as Ceramco (trademark of Johnson & Johnson). This cement has freeze dried polyacrylate (powder) and it is added to the other powder (which is mainly zinc oxide). Instead of adding water to this cement, as is usually done, the present invention contemplates adding thereto a small amount of a saturated aqueous solution of potassium nitrate. The consistency of the mix can obviously be controlled by varying the amount of saturated aqueous solution added thereto. The aforesaid cement, whether freezedried or not, has proved to be an extremely good vehicle for the potassium nitrate pulp capping compound and proceedure, as it applied readily to the desired area, hardens nicely, and "stays put" when placing the overlying restoration. It will be noted that this cement composition comprising potassium nitrate also serves well as a cement for crowns and bridges, since it helps to keep the pulps healthy and the teeth less sensitive to thermal, tactile and chemical stimuli. Obviously, other suitable non-toxic cement compositions, such as glass ionomer, zinc oxyphosate or the like could be used as the vehicle for the potassium nitrate.

Where the compound and method of the present invention has been used under fillings and to cap injured vital pulps, follow-up examination has revealed no evidence of periapical pathology, and the teeth so treated have remained vital. Most of the treated teeth were immediately asymptomatic following the treatment and elimination of local anesthesia. In some cases, a transient period of cold sensitivity existed, which routinely disappeared, either by itself or by application of the potassium nitrate paste described in applicant's aforesaid U.S. Pat. No. 3,863,006.

Although the exact physiological reaction which takes place when potassium nitrate or the like is applied to diseased pulpal tissues is not known, it is thought that the potassium nitrate heals the pulp by restoring fluid balance, and a more normal electrical charge to the pulp tissues. The inflammatory response that develops when connective tissues are insulted is diminished, and healing of the pulpal connective tissues results. When pulp tissues are injured, histamine and other humoral substances are liberated. They signal the inflammatory response which begins with dilation of capillaries and an inflow of fibrinogen. The fibrinogen clots, and walls off the injury. This process causes tissue swelling. In other areas of the body, edematous connective tissues have room to expand, but this is not the case with the dental pulp as it is encased by the calcified walls of dentin. Tissues swelling within the calcified chambers that encase the pulp tissues causes increased intra-pulpal pressure. If this pressure is not abated, the pulpal tissues will go on to become necrotic, and an abscess will ensue. If the tooth has not already abscessed, the present invention is highly effective in the healing of pulp tissues and the elimination of the destructive inflammatory response within the pulp. However, once an alveolar abscess has formed, the present invention is not effective. It has been found that the present invention provides a far more physiological atmosphere for restoration of pulpal health than do treatments conventionally being used, such as calcium hydroxide preparations which, in fact, probably stimulate a pathological response.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. The method of treating pulpitis so as to prevent abscess formation, comprising the following steps:
   (A) removing any decay that exists
   (B) capping the pulp with a viscous mixture that will harden to a cementlike consistency, the essential ingredient of said mixture being potassium nitrate
   (C) permitting said mixture to substantially harden, and
   (D) placing a permanent restoration over said mixture.

2. The method of claim 1 wherein said mixture comprises potassium nitrate in an aqueous solution and a zinc oxide-eugenol paste.

3. The method of claim 2 wherein said mixture comprises by weight approximately 3 parts potassium nitrate in a saturated aqueous solution, 5 parts eugenol, and 40 parts powered zinc oxide.

4. The method of claim 1 wherein said mixture comprises zinc polyacrylate cement and water saturated potassium nitrate.

5. The method of claim 4 wherein said zinc polyacrylate cement is freeze dried.

* * * * *